US012125261B2

(12) United States Patent
Petersen et al.

(10) Patent No.: US 12,125,261 B2
(45) Date of Patent: *Oct. 22, 2024

(54) SYSTEMS AND METHODS FOR PROBABILISTIC SEGMENTATION IN ANATOMICAL IMAGE PROCESSING

(71) Applicant: HeartFlow, Inc., Redwood City, CA (US)

(72) Inventors: Peter Kersten Petersen, Palo Alto, CA (US); Michiel Schaap, Oegstgeest (NL); Leo Grady, Darien, CT (US)

(73) Assignee: HeartFlow, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/817,737

(22) Filed: Aug. 5, 2022

(65) Prior Publication Data

US 2022/0383495 A1    Dec. 1, 2022

Related U.S. Application Data

(63) Continuation of application No. 16/790,037, filed on Feb. 13, 2020, now Pat. No. 11,443,428, which is a
(Continued)

(51) Int. Cl.
*G06T 7/00* (2017.01)
*G06F 18/2415* (2023.01)
(Continued)

(52) U.S. Cl.
CPC ........ *G06V 10/764* (2022.01); *G06F 18/2415* (2023.01); *G06T 7/0014* (2013.01);
(Continued)

(58) Field of Classification Search
CPC . G06T 7/0014; G06T 7/11; G06T 7/13; G06T 7/143; G06T 7/60; G06T 2200/04;
(Continued)

(56) References Cited

U.S. PATENT DOCUMENTS 10,600,181 B2 * 3/2020 Petersen ................. G06T 7/143
11,443,428 B2 * 9/2022 Petersen .................. G06T 7/11
(Continued)

FOREIGN PATENT DOCUMENTS

CA    2320375 C  *  7/2007  .......... G06T 7/0012
EP    2808844 A2    12/2014

OTHER PUBLICATIONS

Corsi et al. "Improved Automated Quantification of Left Ventricular Size and Function from Cardiac Magnetic Resonance Images." Computers in Cardiology, Sep. 17, 2006, pp. 53-56 (Year: 2006).*
(Continued)

*Primary Examiner* — Jon Chang
(74) *Attorney, Agent, or Firm* — Bookoff McAndrews, PLLC

(57) ABSTRACT

Systems and methods are disclosed for performing probabilistic segmentation in anatomical image analysis, using a computer system. One method includes receiving a plurality of images of an anatomical structure; receiving one or more geometric labels of the anatomical structure; generating a parametrized representation of the anatomical structure based on the one or more geometric labels and the received plurality of images; mapping a region of the parameterized representation to a geometric parameter of the anatomical structure; receiving an image of a patient's anatomy; and generating a probability distribution for a patient-specific segmentation boundary of the patient's anatomy, based on the mapping of the region of the parameterized representation of the anatomical structure to the geometric parameter of the anatomical structure.

20 Claims, 4 Drawing Sheets

Related U.S. Application Data continuation of application No. 15/852,119, filed on Dec. 22, 2017, now Pat. No. 10,600,181.

(60) Provisional application No. 62/438,514, filed on Dec. 23, 2016.

(51) Int. Cl.

| | |
|---|---|
| *G06T 7/11* | (2017.01) |
| *G06T 7/13* | (2017.01) |
| *G06T 7/143* | (2017.01) |
| *G06T 7/60* | (2017.01) |
| *G06V 10/764* | (2022.01) |
| *A61B 6/50* | (2024.01) |

(52) U.S. Cl.
CPC .............. *G06T 7/11* (2017.01); *G06T 7/13* (2017.01); *G06T 7/143* (2017.01); *G06T 7/60* (2013.01); *A61B 6/504* (2013.01); *G06T 2200/04* (2013.01); *G06T 2207/20076* (2013.01); *G06T 2207/20081* (2013.01); *G06T 2207/20084* (2013.01); *G06T 2207/30101* (2013.01); *G06T 2207/30104* (2013.01); *G06T 2207/30172* (2013.01)

(58) Field of Classification Search
CPC . G06T 2207/20076; G06T 2207/20081; G06T 2207/20084; G06T 2207/30101; G06T 2207/30104; G06T 2207/30172; G06V 10/764; A61B 6/504; G06F 18/2415
See application file for complete search history.

(56) References Cited

U.S. PATENT DOCUMENTS

| | | |
|---|---|---|
| 2007/0014457 A1 | 1/2007 | Jolly et al. |
| 2012/0027272 A1 | 2/2012 | Akinyemi et al. |
| 2012/0134552 A1 | 5/2012 | Boettger |
| 2015/0359601 A1 | 12/2015 | Sauer et al. |
| 2016/0267673 A1 | 9/2016 | Grbic et al. |

OTHER PUBLICATIONS

Phellan Renzo et al. "Medical image segmentation using object atlas versus object cloud models", Progress in Biomedical Optics and Imaging, SPIE—International Society for Optical Engineering, Belligham, WA, US, vol. 9415, Mar. 18, 2015, pp. 94151M-94151M.

Mao et al. "Segmentation of Carotid Artery in Ultrasound Images." Proceedings of the 22nd Annual EMBS International Conference, Jul. 23, 2000, pp. 1734-1737 (Year: 2000).

Nejati, Alireza, et al. "Improving active contour methods for tracking endothelial cells by the removal of low-confidence edge segments." Annual International Conference of the IEEE Engineering in Medicine and Biology Society. IEEE, 2012.

* cited by examiner

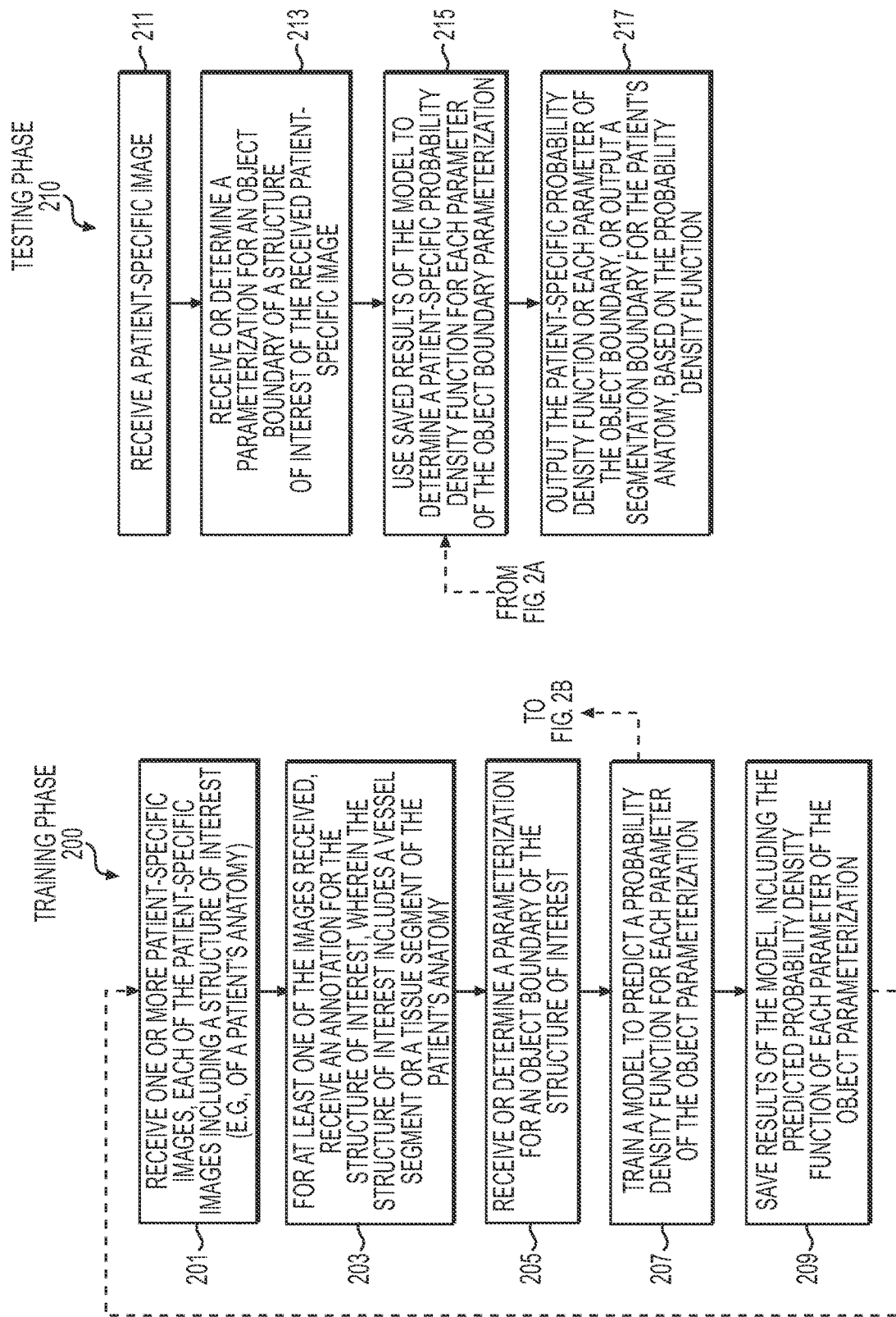

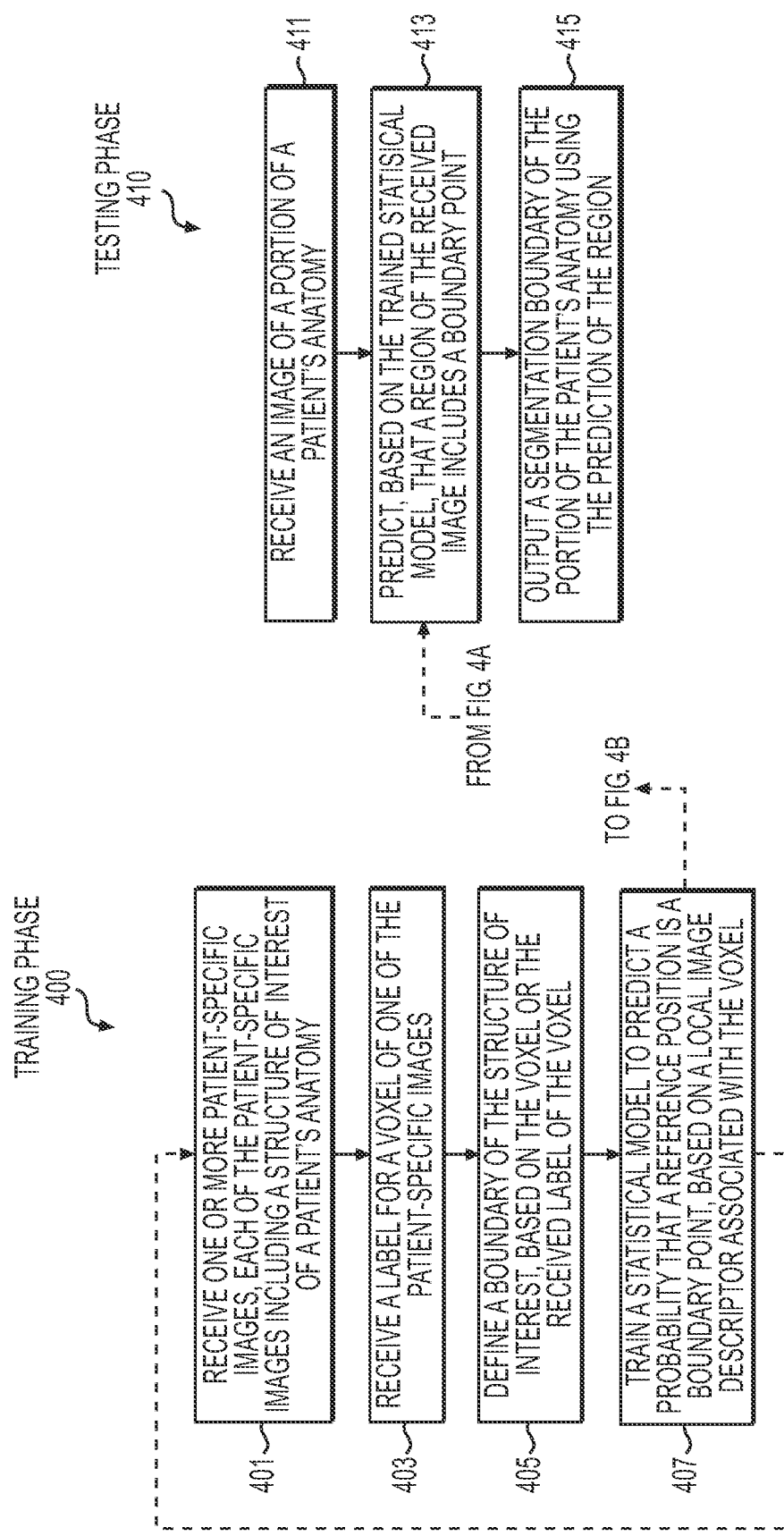

SYSTEMS AND METHODS FOR PROBABILISTIC SEGMENTATION IN ANATOMICAL IMAGE PROCESSING

RELATED APPLICATION(S)

This application is a continuation of U.S. application Ser. No. 16/790,037, filed Feb. 13, 2020, issued as U.S. Pat. No. 11,443,428 on Sep. 13, 2022, which is a continuation of U.S. application Ser. No. 15/852,119, filed Dec. 22, 2017, issued as U.S. Pat. No. 10,600,181 on Mar. 24, 2020, which claims the benefit of priority to U.S. Provisional Application No. 62/438,514 filed Dec. 23, 2016, disclosures of which are hereby incorporated by reference in their entireties.

FIELD OF THE INVENTION

Various embodiments of the present disclosure relate generally to medical imaging and related methods. More specifically, particular embodiments of the present disclosure relate to systems and methods for performing probabilistic segmentation in anatomical image analysis.

BACKGROUND

One type of medical image analysis involves decomposing an image into meaningful regions, e.g., imaged anatomical structures versus image artifacts. This process is sometimes referred to as (medical) image segmentation. In some cases, the presence of image noise or other image artifacts may hinder accurate segmentation of anatomical structures of interest. A common approach for automating segmentation may include using a learning based system. A learning based system may be trained to predict a class label probability for each image element (e.g., pixel, voxel, or object parameter). For instance, a shape may be fitted, or a structured output model may be applied to assign a label to each image element based on its predicted label probability. A learning based system may also be trained to estimate, for an image, the locations of boundaries of different structures within the image. In some cases, these estimated boundaries may not align with the boundaries between discrete image elements. The final segmentation may reflect a likely segmentation for a given image.

However, many segmentation boundary locations may be plausible. Even human technicians may select or draw different boundary locations due to ambiguous image data. In addition, boundaries estimated by a trained system may be ambiguous due to a lack of appropriate training examples or due to a sub-optimally trained method. In this case, the trained system may not provide accurate object boundaries. A final segmentation often does not indicate whether the segmentation is a nearly definite accurate representation of a portion of anatomy, or whether an alternative segmentation is almost equally likely to render an accurate representation of anatomy. Further, the final segmentation may not indicate region(s) where the final segmentation boundary was more certain or less certain. Accordingly, a desire exists to understand the statistical confidence (or statistical uncertainty) of a provided segmentation. A desire also exists for generating alternative or aggregated solutions segmentations.

The present disclosure is directed to overcoming one or more of the above-mentioned problems or interests.

SUMMARY

According to certain aspects of the present disclosure, systems and methods are disclosed for performing probabilistic segmentation in image analysis. One method of performing probabilistic segmentation in anatomical image analysis includes: receiving a plurality of images of an anatomical structure; receiving one or more geometric labels of the anatomical structure; generating a parameterized representation of the anatomical structure based on the one or more geometric labels and the received plurality of images; mapping a region of the parameterized representation to a geometric parameter of the anatomical structure; receiving an image of a patient's anatomy; and generating a probability distribution for a patient-specific segmentation boundary of the patient's anatomy, based on the mapping of the region of the parameterized representation of the anatomical structure to the geometric parameter of the anatomical structure. In accordance with another embodiment, a system for performing probabilistic segmentation in anatomical image analysis comprises: a data storage device storing instructions for performing probabilistic segmentation in anatomical image analysis; and a processor configured for: receiving a plurality of images of an anatomical structure; receiving one or more geometric labels of the anatomical structure; generating a parameterized representation of the anatomical structure based on the one or more geometric labels and the received plurality of images; mapping a region of the parameterized representation to a geometric parameter of the anatomical structure; receiving an image of a patient's anatomy; and generating a probability distribution for a patient-specific segmentation boundary of the patient's anatomy, based on the mapping of the region of the parameterized representation of the anatomical structure to the geometric parameter of the anatomical structure.

In accordance with yet another embodiment, a non-transitory computer readable medium for use on a computer system containing computer-executable programming instructions for performing a method of probabilistic segmentation in anatomical image analysis is provided. The method includes: receiving a plurality of images of an anatomical structure; receiving one or more geometric labels of the anatomical structure; generating a parameterized representation of the anatomical structure based on the one or more geometric labels and the received plurality of images; mapping a region of the parameterized representation to a geometric parameter of the anatomical structure; receiving an image of a patient's anatomy; and generating a probability distribution for a patient-specific segmentation boundary of the patient's anatomy, based on the mapping of the region of the parameterized representation of the anatomical structure to the geometric parameter of the anatomical structure.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 2A and 2B are flowcharts of an exemplary method for performing probabilistic segmentation using parameterized object boundaries, according to an exemplary embodiment of the present disclosure.

FIGS. 4A and 4B are flowcharts of an exemplary embodiment of the method for performing probabilistic segmentation using local image descriptors, according to an exemplary embodiment of the present disclosure.

DESCRIPTION OF THE EMBODIMENTS

Figure 1:
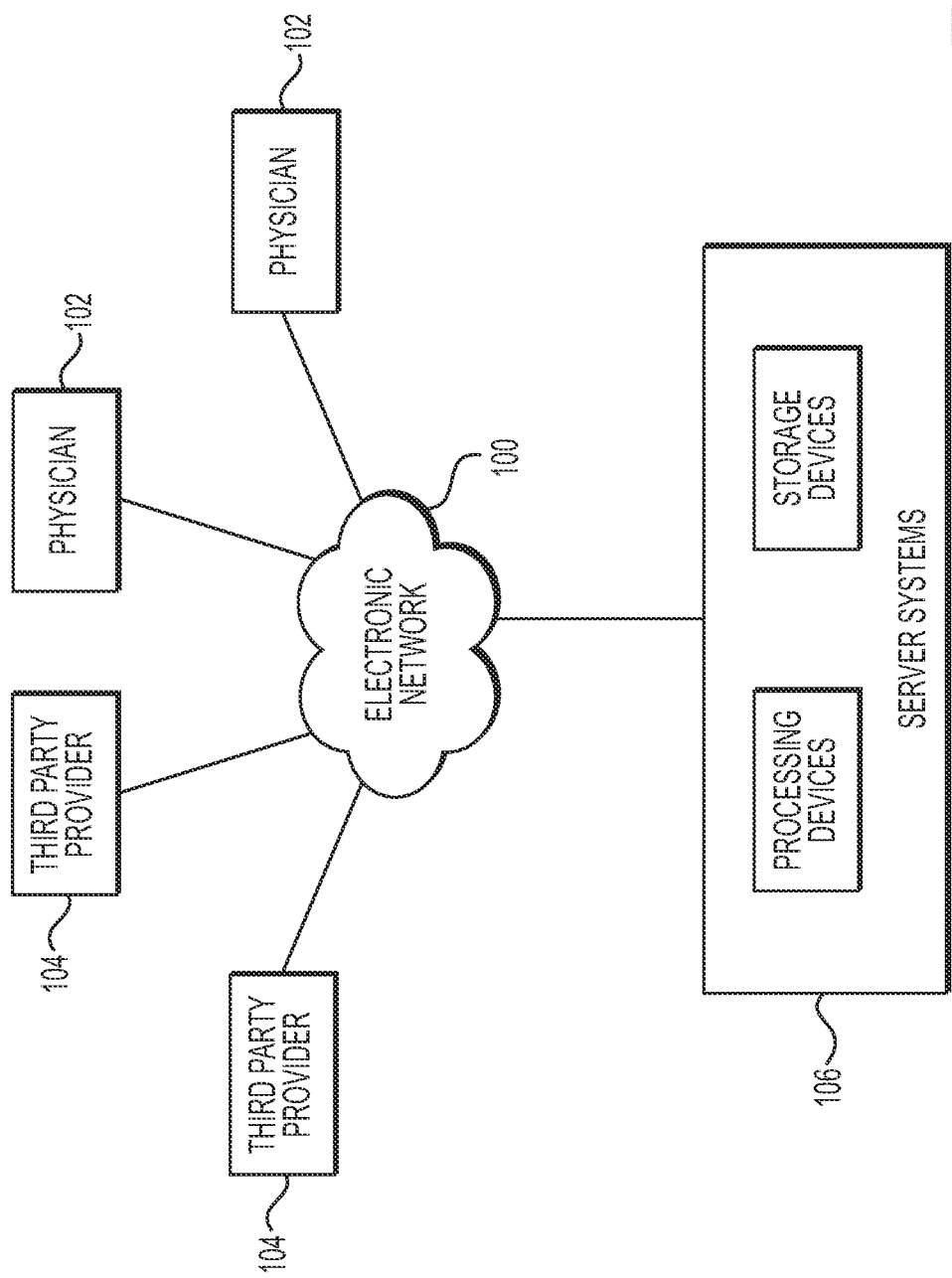
FIG. 1 is a block diagram of an exemplary system and network for performing probabilistic segmentation in image analysis, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

As described above, medical image segmentation may involve rendering various segmentation boundary locations. Often, a final segmentation includes a likely segmentation or boundary for an object of interest (e.g., an anatomical structure) represented in a given image. However, many other segmentation boundary locations may be plausible as well. While class label probability for image elements used in segmentation may be post-processed, a desire exists to understand the confidence or uncertainty of a final segmentation. Further, a desire exists to provide alternative solution(s) to the final segmentation.

The present disclosure is directed to providing information on the statistical confidence or statistical uncertainty of a segmentation by predicting a probability distribution of segmentation boundary locations. In one embodiment, the present disclosure may include both a training phase and a testing (or usage or production) phase to estimate a segmentation boundary and/or probability density function for the segmentation boundary. For example, the disclosed systems and methods may be applied to segmenting anatomy in received image(s) of a patient of interest and determining the probability density function for the boundary of the segmented anatomy. In one embodiment, the training phase may include developing a set of probability density functions for at least one parameter of an object parameterization associated with received images. For example, the training phase may involve receiving a collection of images, receiving or inputting information of an anatomical part or portion shown in each of the images (e.g., a localized anatomy for each of the images), defining a parameterization the anatomical part or portion, and generating a probability density function for each parameter of the parameterization, based on the received information. An output from the training phase may include a probability density function for each parameter of an anatomical or medical model.

In one embodiment, a testing phase may include receiving images of a patient's anatomy. The patient may be a patient of interest, e.g., a patient desiring a diagnostic test. The testing phase may involve completing a segmentation (e.g., rendering a segmentation boundary or surface reconstruction) of the patient's anatomy based on the received images and using the stored training phase probability density function(s) to compute a patient-specific probability density function for a parameter of the completed segmentation. As used herein, the term "exemplary" is used in the sense of "example," rather than "ideal." Although this exemplary embodiment is written in the context of medical image analysis, the present disclosure may equally apply to any non-medical image analysis or computer vision evaluation.

Referring now to the figures, FIG. 1 depicts a block diagram of an exemplary environment of a system and network for performing probabilistic segmentation. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' cardiac, vascular, and/or organ systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular/organ images and/or patient-specific information to server systems 106 over the electronic network 100. Server systems 106 may include storage devices for storing images and data received from physicians 102 and/or third party providers 104. Server systems 106 may also include processing devices for processing images and data stored in the storage devices. Alternatively or in addition, the probabilistic segmentation of the present disclosure (or portions of the system and methods of the present disclosure) may be performed on a local processing device (e.g., a laptop), absent an external server or network.

Figures 3A, 3B:
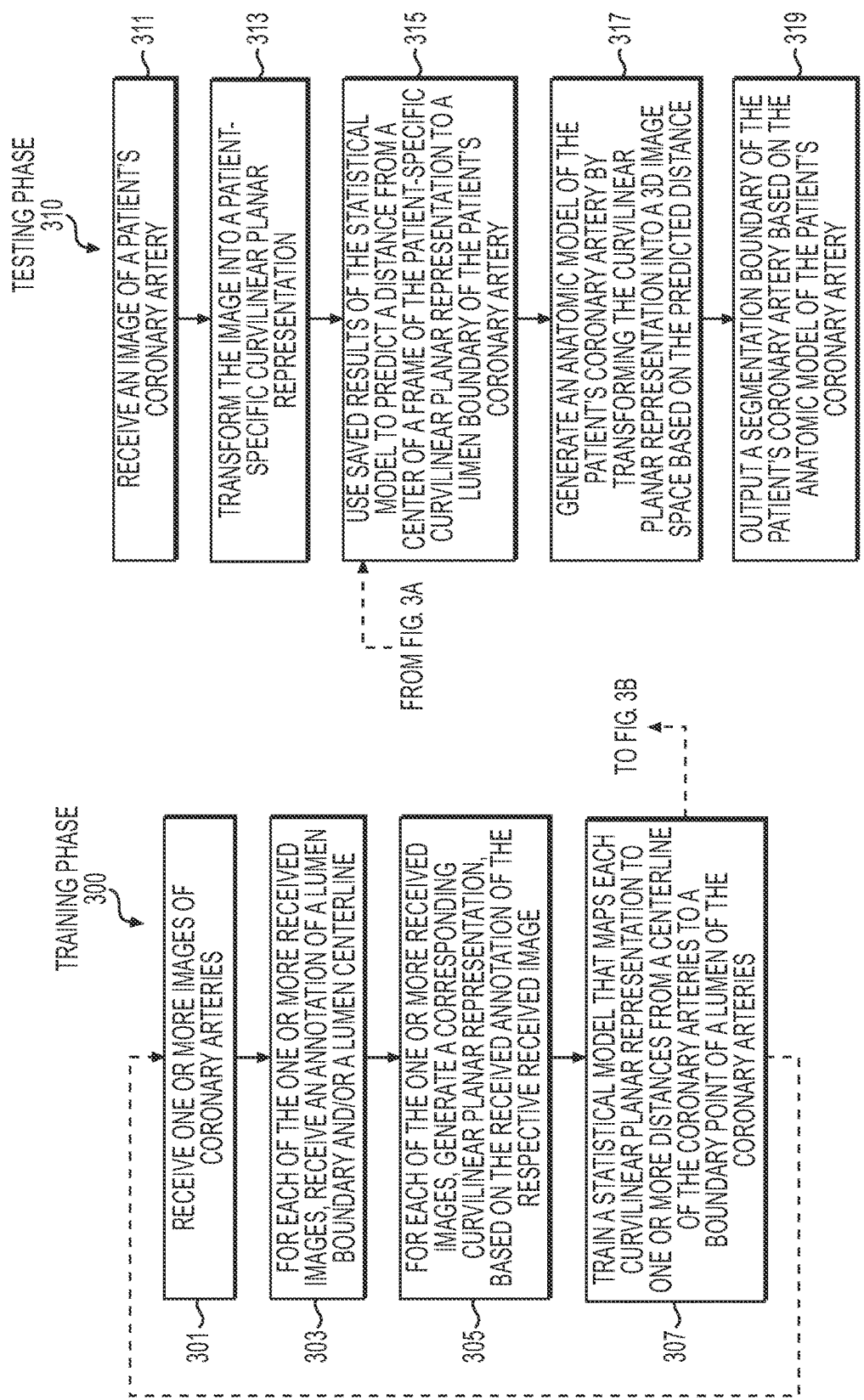
FIGS. 3A and 3B are flowcharts of an exemplary embodiment of the method of FIGS. 2A and 2B, as applied to probabilistic segmentation of blood vessels, according to an exemplary embodiment of the present disclosure.

FIGS. 2A and 2B describe one embodiment for performing probabilistic segmentation using a learning system trained with parameterized object boundaries. FIGS. 3A and 3B are directed to specific embodiments or applications of the methods discussed in FIGS. 2A and 2B. For example, FIG. 3A and FIG. 3B describe an embodiment for the probabilistic segmentation of blood vessels using a learning system trained on parameterized object boundaries. FIGS. 4A and 4B describe another probabilistic segmentation method which employs a learning system trained using local image descriptors. In contrast to the methods of FIGS. 2A and 2B, the methods of FIGS. 4A and 4B permit segmenting an image without a regressor or simplifying transformation. All of the methods may be performed by server systems 106, based on information, images, and data received from physicians 102 and/or third party providers 104 over electronic network 100.

FIGS. 2A and 2B describe an embodiment for predicting and testing a probability density function. Understanding a probability density function in association with a segmentation may be helpful for understanding whether the resulting segmentation is reliable, or whether portion(s) of the resulting segmentation are possibly inaccurate. Since analyses may be performed based on the segmentation, the present disclosure may provide an understanding of where or how the analyses could be inaccurate due to the segmentation. For example, accuracy of segmentation of a large vessel may impact blood flow analyses, whereas accuracy of segmentation in a small downstream vessel may have little influence on the accuracy of a predicted blood flow value. A probability density function could help determine whether to use a segmentation for an analysis, or which part of a segmentation could be used reliably for an analysis.

In one embodiment, probabilistic segmentation may include two phases: a training phase and a testing phase. The training phase may involve training a learning system (e.g., a deep learning system) to predict a probability density function (PDF) for a parameter of a segmentation/object parameterization. The testing phase may include predicting a probability density function for a parameter of an object parameterization of a newly received image.

FIG. 2A is a flowchart of an exemplary training phase method 200 for training a learning system (e.g., a deep learning system) to predict a probability density function, according to various embodiments. Method 200 may provide the basis for a testing phase or production phase in method 210 of FIG. 2B, for the probabilistic segmentation of an imaged object of interest of a specific patient. In one embodiment, step 201 of method 200 may include receiving one or more images in an electronic storage medium (e.g., hard drive, network drive, cloud drive, mobile phone, tablet, database, etc.). In a medical context, these images may, for instance, be from a medical imaging device, e.g., computed tomography (CT), positron emission tomography (PET), single-photon emission computerized tomography (SPECT), magnetic resonance imaging (MRI), microscope, ultrasound, (multi-view) angiography, etc. In one embodiment, multiple images for a single patient may be used. In a further embodiment, the images may comprise a structure of a patient's anatomy. In other embodiments, the images may be of numerous individuals having similar anatomical features or numerous individuals having different anatomical features. In a non-medical context, these images may be from any source, e.g., a camera, satellite, radar, lidar, sonar, telescope, microscope, etc. In the following disclosure, images received in step 201 may be referred to as, "training images."

In one embodiment, step 203 may include receiving an annotation for one or more structures of interest shown in one or more of the training images. In one embodiment, all training images may be annotated. This type of embodiment may be referred to as, "supervised learning." Another embodiment may include only a subset of the training images with annotations. This type of scenario may be referred to as, "semi-supervised learning." In one embodiment, the structures of interest may include a blood vessel or tissue of the patient. In such a case, annotation(s) may include labels for vessel names (e.g., right coronary artery (RCA), left anterior descending artery (LAD), left circumflex artery (LCX), etc.), vessel landmarks (e.g., aortic valve point, ostia points, bifurcations, etc.), estimated vessel location, flags (e.g., noted portions where imaging is ambiguous or boundaries or unclear), etc.

In one embodiment, step 205 may include defining a parameterization for an object boundary of the structure of interest. For example, step 205 may include defining whether to generate an implicit or an explicit surface representation as an object boundary of the structure of interest. Defining the object boundary of the structure of interest may include subdividing the structure of interest into one or more portions and estimating the boundary of each of the portions. Alternately, the structure of interest may be subdivided into one or more segments, and the boundary of each of the segments may be estimated. Estimating the boundary may include estimating the location of the structure (or a surface representation of the structure), for example, by estimating the probability that a certain image region or voxel includes a representation of the structure.

One such scenario may involve receiving an image of a group of people. A person's face may be defined as the structure of interest and step 205 may include defining a desired parameterization for the person's face. For example, the desired parameterization may include a 3D surface model of the person's face. Step 205 may include generating an object boundary of the person's face as a 3D surface model. For instance, step 205 may include defining a point in the image and estimating a probability that the point is part of the portion of the image showing the face. Once probability estimates are computed for multiple points, portions of the image showing the person's face may be distinguished from portions of the image that do not show the person's face. In one embodiment, extracting a parameterization of an object of interest comprising a face may include receiving annotations for locations of facial landmarks (e.g., eyes, the point of the nose, the corners of the mouth, etc.). Each of the landmarks K may be represented by a 2D position in a given image. The 2D positions of each of the landmarks may be concatenated in a single K*2 dimensions vector, where the vector may be used as a parameterization of the face. A 3D surface model of the person's face may be constructed from the generated probabilities and the image. In one embodiment, the 3D surface model of the person's face may constitute an object boundary.

As another scenario, step 205 may include defining a parameterization for an object boundary of a left ventricle myocardium. In such a case of myocardium segmentation, step 205 may include receiving a series of labeled cardiac computed tomography angiography (CTA) images, where each image voxel may be labeled as being inside or outside the left ventricle myocardium. Step 205 may then further include deforming the received images into a common space with elastic image registration and recording the transformation for each image (Ti). Then, a set of K points may be distributed over the surface of the annotated myocardium in the common space, and the inverse transformation ($Ti^{-1}$) may be used to deform the set points back to the original image space. Lastly, the K 3D points may be concatenated into a K*3 dimensional vector and used as a parameterization of the left ventricle myocardium.

In a case involving lumen segmentation, step 205 may include defining a parameterization for an object boundary of a vessel lumen. In such a scenario, step 205 may include receiving a surface model for the vessel lumen and a set of paths (e.g., centerlines) defining the approximate location of the center of the vessel. Then, for each cross-sectional image, step 205 may include defining a set of K rays extending from the vessel centerline, where the K rays comprise equal angularly distributed rays in the plane cross-sectional to the centerline. These rays may be intersected with the surface model of the lumen and the distance from the centerline to the intersection point may be recorded. These K distances may be concatenated in a K dimensional vector and used as the parameterization of a cross-sectional vessel shape.

Alternately or in addition, the parameterization of the object boundary may include estimating the location of an object other than the structure of interest or estimating the object boundary using a parameter that is not on the boundary or surface of the structure of interest. For example, if a blood vessel is the structure of interest, parameterization of the object boundary using an indication of the object boundary may include estimating a centerline location. As a more general example, the parameterization may be performed by estimating the location of medial axes. Medial axes may include a set of points of the structure of interest that have multiple closest points on the structure's boundary. For example, a medial axis may connect several points that are equidistant to more than one point on the structure's boundary. Rather than existing on the surface of the structure (e.g., at the structure's boundary), medial axes may exist inside the boundaries/surfaces of the structure. In other words, the medial axes may form a skeleton for the structure of interest. Parameterization using a medial axes may also include finding, for at least one point on the medial axes, a distance from the point to the boundary of the structure of interest. Overall, step 205 may include defining a desired type of parameterization for the object boundary of a structure of interest, as well as estimating (or parameterizing) the object boundary of the structure of interest.

In one embodiment, step 207 may include training a model to predict a probability density function (PDF) for the object boundary parameterization of the training data (e.g., images and annotations of steps 201 and 203). For example, the training may predict a PDF of a joint distribution of the object boundary parameterization, a PDF for each parameter of the object boundary parameterization, etc. A variety of machine learning techniques may be used to train the model.

For example, training the model may include approximating the PDF of a parameter of the object boundary parameterization by using a mixture model (e.g., using a mixture density model). For instance, an object boundary may be assumed as represented by a set of landmark points. The landmark points may indicate a point estimate for a distance from a given input location (e.g., the center of an input patch) to the object boundary in a given direction. In one embodiment, the input patch may be comprised of a 2D frame of a curvilinear planar representation (e.g., a 2D rectangle extracted roughly orthogonal to the direction of a vessel centerline). Step 207 may include training a model to predict a point estimate/value for the distance, as well as determining a statistical value indicating the certainty of the predicted distance value.

For example, determining the statistical value may include modeling a statistical uncertainty in the distance value using a mixture of Gaussians (MoG). In one scenario, step 207 may include training a model to learn to predict weighting coefficients, mean values, and standard deviations to describe the MoG. The MoG may be combined with a neural network structure in the form of a mixture density network (MDN). In one embodiment, the combined MoG and neural network structure may be optimized with a backpropagation algorithm using stochastic gradient descent. The optimization may include optimizing toward any of several local minima (rather than a global optimum). The local minimum that is reached (out of the several local minima) may be dictated by many factors, e.g., the neural network structure, the parameter initialization, the learning schedule, the type of optimization, etc. Any machine learning technique that is able to predict a multi-variate output (e.g. variants of deep learning, support vector machine, random forests, etc.) could be applied in this optimization step. In the case of a MoG or MDN, the conditional mean (e.g., expected or ideal value) may be optimized to approximate the distance from the input patch to the object boundary.

As another example, step 207 of training a model to predict a PDF may include approximating a PDF by modeling a distribution for latent variables and sampling multiple predictions from the modeled distribution. For example, training the model may include approximating PDF variational models (e.g., semi-supervised variational autoencoders). These PDF variational models may predict object boundary parameters, based on randomly sampled input parameters. The PDF variational models may also be conditioned on image feature values. In one scenario, the spread of these predictions may be summarized by a standard deviation. In one embodiment, such a standard deviation may represent the level of uncertainty of one or more segmentations of the object boundary. Accordingly, step 207 may include training a model to predict a PDF by computing standard deviations as described above. Step 209 may include saving the results of the model, including the predicted PDF of each parameter of the object parameterization, e.g., to a physical data storage device, cloud storage device, etc.

FIG. 2B is a block diagram of an exemplary testing phase (or usage or "production phase") method 210 for predicting the certainty of a segmentation for a specific patient image, according to an exemplary embodiment of the present disclosure. In one embodiment, the uncertainty of the segmentation may be predicted using a trained model (e.g., from method 200). The uncertainty may be conveyed by a probability density function.

In one embodiment, step 211 may include receiving one or more medical images in an electronic storage medium (e.g., hard drive, network drive, cloud drive, mobile phone, tablet, database, etc.). In one embodiment, the images may include medical images, e.g., images may be from any medical imaging device, e.g., CT, MR, SPECT, PET, microscope, ultrasound, (multi-view) angiography, etc. In one embodiment, training images (e.g., of method 200) may include images acquired from one patient, and step 211 may include receiving images also of that one patient. Alternately or in addition, step 211 may include receiving one or more images from a non-medical imaging device, e.g., a camera, satellite, radar, lidar, sonar, telescope, microscope, etc. In the following steps, images received during step 211 may be referred to as "testing images" or "production images."

In one embodiment, step 213 may include initializing the trained model (of method 200) for use on the patient-specific image of step 211. For example, the trained model may predict a PDF for a parameter of an object parameterization of a structure of interest. Step 213 may include initializing the trained model by providing an object parameterization for the trained model's PDF prediction. For example, step 213 may include receiving an estimate of the segmentation boundary or an estimate of the location or boundary of another object. In other words, as a preliminary step to reduce the search space of plausible segmentations, a known segmentation algorithm may be applied to (patient-specific) image(s) of step 211. For example, an object boundary of a structure of interest in the patient-specific image(s) may be approximated by its medial axis (e.g., a centerline), using a centerline extraction algorithm from the literature.

In one embodiment, step 215 may include using the trained model to predict a PDF for a parameter of the object parameterization. For instance, if an MDN is used, the predictions may describe the parameters of a mixture of Gaussians which may approximate the PDF. For example, an MDN may be optimized during training (e.g., method 200) to match the training data. Then, during testing, the trained model may predict the MDN that best matches the received patient-specific image(s). In one embodiment, step 215 may include using the trained model to predict the PDF for each parameter of the object parameterization.

In one embodiment, step 217 may include selecting a representative value from the PDF for a parameter of the object parameterization. This step may be performed with any number of standard methods, e.g., maximum a posteriori, maximum likelihood, etc. Alternately or in addition, step 217 may include resolving a complete segmentation boundary based on the PDF. In one embodiment, resolving a complete segmentation boundary may be performed using surface reconstruction. For instance, a 3D surface reconstruction algorithm (e.g., Poisson surface reconstruction) may be used to reconstruct a surface from a cloud of predicted segmentation boundary locations. Specific variants of a 3D surface reconstruction algorithm can be designed that fully utilize the PDF without first selecting a representative value from the PDF. For example, one embodiment could include using an algorithm similar to a mean-shift mode finding algorithm comprising an iterative process of reconstructing the boundary and refining the PDF. Alternately or in addition, an initial representative value may be selected, surface reconstruction may be performed with a known reconstruction technique, and the PDF may be reweighted based on how closely the PDF resembles the reconstructed surface. This process may be repeated until convergence. The advantage of this process is that locally incorrect estimates of the PDF may be corrected by the global nature of the surface reconstruction technique. For example, given a PDF indicating locally that the distance from the centerline to the lumen boundary has a chance of 40% to be 2 mm and 60% to be 3 mm, but all surrounding distances are predicted to be 3 mm with 100% certainty, a current approach may result in a prediction of 2 mm for the single (local) point and 3 mm for the surrounding portions of the lumen. In the approach outlined above including iterative reweighting, however, 2 mm may be the prediction for the local point in an early iteration, but calculations may quickly converge to a prediction of 3 mm because of the neighboring distances. If the structure of interest exhibits a certain (e.g., known) structure or geometry, this structure and geometry may serve as prior knowledge to constrain the space of possible reconstructions. For instance, tubular structures may be represented by a set of ellipse landmarks along a centerline.

In one embodiment, step 217 may include outputting one or both of the complete segmentation boundary and/or the predicted PDF for one or more parameters of the object parameterization. The output may be stored in an electronic storage medium (e.g., hard drive, network drive, cloud drive, mobile phone, tablet, database, etc.) and/or displayed (e.g., via an interface, screen, projection, presentation, report, dashboard, etc.).

Computed PDFs may have several applications or uses. For example, a PDF may be used to compute a confidence score (e.g., by computing a conditional standard deviation). In one embodiment, step 217 may include outputting the confidence score to an electronic display and/or an electronic storage device (hard drive, network drive, cloud storage, portable disk, etc.). The confidence score may be used in multiple ways. In one embodiment, the confidence score or samples from the PDF may be used to guide a human expert or computational algorithm to focus on uncertain or ambiguous image/model/segmentation regions that may be analyzed more exhaustively. For example, regions of a segmentation boundary (e.g., object boundary of a structure of interest) that have confidence scores below a predetermined threshold score may be highlighted in a visual display.

In one scenario, regions of a segmentation boundary that have confidence scores below a predetermined threshold score may be prioritized in a sequence of displays prompting user validation of the segmentation. Prioritization of the display of the regions may include displaying the low-confidence regions for validation, prior to displaying regions with higher confidence scores. Higher confidence scores may be defined as confidence scores exceeding the predetermined threshold score. For one case, a model validation workflow may display regions of a segmentation boundary based on the lowest to the highest confidence scores. For example, the workflow may prompt a technician to examine or validate regions of a segmentation boundary that have the lowest confidence scores, prior to reviewing regions of the boundary with higher confidence scores. One exemplary workflow may alert the technician only to regions of the segmentation boundary that have confidence scores below a predetermined threshold score. Alternately or in addition, the display may highlight portions with high confidence scores and offer only these portions as segments of the model that may be used for diagnostic evaluations.

In one embodiment, computed confidence score or samples from the PDF may also be used as a probabilistic input for determining physiological/biomechanical properties at one or more locations in a vascular or organ/muscle model (e.g., a blood flow characteristic including flow, velocity, pressure, fractional flow reserve (FFR), instantaneous fractional flow reserve (iFFR), axial stress, wall shear stress, strain, force, shape, size, volume, tortuosity, etc.). These physiological or biomechanical properties may be determined via biophysical simulation, machine learning, association with a database, etc. For example, the uncertainty of lumen boundary points may be used to model variations of the lumen geometry. The modeled variations of lumen geometry may be utilized by a machine-learning driven FFR method. For instance, if a vessel size is uncertain at a particular location, the PDF may provide capabilities to compute an uncertainty of FFR (axial stress, iFFR, etc.) computed based on the uncertain vessel size. In this way, the PDF may provide an understanding of confidence interval or probability density functions of physiological/biomechanical properties computed based on a segmentation boundary (with a predicted PDF). The probabilistic segmentation model and the biophysiological model could be trained in sequence or simultaneously in one end-to-end approach.

The confidence score may further be used as an input for a segmentation algorithm for weighting the training data. For example, training may include sampling certain training samples (e.g., training segmentations with a high degree of accuracy for the structure of interest) at a different frequency or at different iterations than uncertain training examples (e.g., training segmentations with a low degree of accuracy for the structure of interest). The confidence score may help determine which sets of training data should have more impact on the training of the probability density function model (e.g., of method 200).

The confidence score may also be used to quantify the quality of a reconstruction algorithm. Quantifying the quality of a reconstruction algorithm may provide indication of a preferred segmentation. For instance, a preferred reconstruction algorithm may include a reconstruction algorithm that produces an image which leads to a more certain segmentation over image(s) produced by other reconstruction algorithms. Similarly, for various models, the confidence score may be used to select among different parameterized models. A model (e.g., a complete segmentation boundary) with higher confidence in a segmentation may be preferred. In one embodiment, multiple different models may also be presented to a user for review and/or selection, possibly with the guidance of the confidence score information. Lastly, the PDF or confidence score may be used to build an integrated model/integrating multiple images to produce a resultant model/image, reconstruction, or enhancement that meets or exceeds a given, target PDF or confidence score.

FIGS. 3A and 3B are directed to specific embodiments or applications of the exemplary methods discussed in FIGS. 2A and 2B. For example, FIG. 3A and FIG. 3B, respectively, describe an exemplary training phase and testing phase for performing probabilistic segmentation of blood vessels. The accuracy of patient-specific segmentation of blood vessels may impact several medical assessments, including blood flow simulations, calculations of geometric characteristics of blood vessels, plaque rupture predictions, perfusion predictions, etc. While a single segmentation output of a blood vessel may be provided by automated algorithms, several uncertainties may exist about the precise location of a segmentation boundary. Even two human experts may favor different annotations of a vessel boundary due to ambiguous image content. In one embodiment, method 300 may model the uncertainty (or the confidence) in a generated vessel segmentation boundary by modeling a probability density function (PDF) around the vessel segmentation boundary. Such a probabilistic segmentation model could be applied to model the uncertainty of plaque, tissue, organ or bone segmentation, where the segmentation model may capture multiple plausible segmentation realizations or summarize the variability of the model.

FIG. 3A is a flowchart of an exemplary method 300 for a training phase designed to provide the basis for performing probabilistic segmentation of a patient's blood vessels, according to various embodiments. In one embodiment, step 301 may include receiving one or more images of coronary arteries in an electronic storage medium (e.g., hard drive, network drive, cloud drive, mobile phone, tablet, database, etc.). These images may, for instance, be from a medical imaging device, such as CT, MR, SPECT, PET, ultrasound, (multi-view) angiography, etc. These images may be referred to as "training images."

In one embodiment, step 303 may include receiving annotations of the vessel lumen boundary and the vessel lumen centerline(s) of each of the training images. For example, step 303 may include receiving or generating a geometric mesh of the coronary vessels represented in the received images. In one embodiment, the geometric mesh may be specified as a set of vertices and edges. Alternately or in addition, step 303 may include receiving a centerline of the coronary vessels. The centerline may also be represented as a set of vertices that may be connected by edges.

In one embodiment, step 305 may include transforming the training image data (e.g., the geometric mesh, vertices, edges, centerline, etc.) into a curvilinear planar representation (CPR). For example, a set of planes (e.g., frames) may be extracted along the centerline (e.g., orthogonal to the centerline) to constitute a 3D volume. In one embodiment, the 3D volume may comprise a curvilinear planar representation (CPR), with a coordinate system frame of reference defining two dimensions and the centerline length defining a third dimension. In one embodiment, the curvilinear planar representation may eliminate degrees of freedom (e.g., the curvature of the centerline), which may not be relevant for predicting one or more parameters of the coronary vessels. For example, the curvature of the centerline may be irrelevant for determining a parameter related to the location of the coronary vessels' lumen boundary.

In one embodiment, step 307 may include training a statistical model that may map the CPR or sub-regions of the CPR to one or more distances from the centerline to boundary points of the lumen. For instance, one such exemplary distance may include the distance from the center of each CPR frame to the lumen boundary in a set of angular directions around the centerline. To model the uncertainty around each distance output, step 307 may include assuming a mixture of Gaussian (MoG) model. In one embodiment, the trained statistical model may predict a set of standard deviations and mixing coefficients for each distance output. The standard deviations and mixing coefficients may approximate the PDF by a mixture of normal distributions. The objective function of the statistical model may be specified, in one embodiment, as the loss between each annotated distance from the centerline to the lumen and the conditional mean of the MoG model. In one embodiment, the objective function for the MoG model may be uniquely defined, and the condition mean of the MoG model may be comprised of a weighted mean. For example, the MoG may provide one or more means, and weights corresponding to each of the means may be determined based on mixing coefficients of the mixture model.

FIG. 3B is a block diagram of an exemplary method 310 for a testing phase that may provide a probabilistic segmentation of a patient's blood vessels, according to one embodiment. In one embodiment, step 311 may include receiving image data of a patient's coronary artery in an electronic storage medium (e.g., hard drive, network drive, cloud drive, mobile phone, tablet, database, etc.).

In one embodiment, step 313 may include transforming the received image data into a curvilinear planar representation (CPR). For instance, step 313 may include receiving a prediction of the centerline of the patient's coronary artery (e.g., from any centerline detection algorithm of the literature). A set of planes may be extracted along the centerline (e.g., orthogonal to the centerline) to include a 3D volume (e.g., CPR) with the coordinate system frame of reference defining two dimensions and the centerline length defining the third dimension. The transformation parameters (e.g., translation, scale, rotation) may be stored.

In one embodiment, step 315 may include using saved results of the training phase (of method 300) to predict distances from the center of each CPR frame to a lumen boundary in the angular directions around a centerline, specified during the training. Alternately or in addition, step 315 may include using saved results of the training phase to predict standard deviation(s) and mixing coefficient(s) for each predicted distance. As a further embodiment, step 315 may include computing a conditional mean and/or a conditional standard deviation of each estimated lumen boundary. In one embodiment, the conditional mean of an estimated lumen boundary may include the location of a landmark point on a lumen mesh. A conditional standard deviation may indicate the uncertainty of the location of the landmark point.

In one embodiment, step 317 may include generating an anatomic model of the patient's imaged coronary artery. The anatomic model may include a final lumen segmentation. For example, step 317 may include transforming the predicted landmark point(s) from the CPR representation back to the original 3D image space. The orientation and position of each frame along the centerline may be determined from the creation of a CPR (if stored during step 313). In one embodiment, the 3D points may be computed from the CPR, and any 3D surface reconstruction method (e.g., Poisson surface reconstruction) may be applied to this point cloud of landmark point(s) to construct the anatomic model or final lumen segmentation.

In one embodiment, step 319 may include outputting the anatomic model/complete segmentation boundary of the vessels and the associated uncertainty values to an electronic storage medium (e.g., hard drive, network drive, cloud drive, mobile phone, tablet, database, etc.) and/or display.

FIGS. 4A and 4B describe a probabilistic segmentation method which uses a learning system trained using local image descriptors. This type of probabilistic segmentation may take place without a regressor or image transformation. In one embodiment, the location of a boundary point may be uncertain, meaning image elements in the neighborhood of the boundary point may be viable alternative candidates. In one embodiment, a segmentation model may be trained to assign probabilities to the likelihood that an element of an image includes an object boundary point. The probabilities in the local neighborhood of the element may then be interpreted as the uncertainty or confidence of the lumen boundary point. One such segmentation model (e.g., statistical method) may include a model trained to classify object boundary points in an image (e.g., in a 3D volume). The classification of the object boundary points may be based on local image descriptors of the image. Examples of local image descriptors may include local image intensities, Gaussian derivative image features, Gabor filter responses, learned features from pre-trained artificial neural network(s), etc.

FIG. 4A provides an exemplary training phase for this type of segmentation model, and FIG. 4B describes an embodiment of testing this segmentation model. FIG. 4A is a flowchart of an exemplary method 400 for a training phase designed to provide a probabilistic segmentation model based on local image descriptors, according to various embodiments. In one embodiment, step 401 may include receiving one or more images of an object of interest in an electronic storage medium (e.g., hard drive, network drive, cloud drive, mobile phone, tablet, database, etc.). These images may, for instance, be from a medical imaging device, e.g., CT, MR, SPECT, PET, ultrasound, (multi-view) angiography, etc. The images may include images of a patient's anatomy. These images may be referred to as "training images."

In one embodiment, step 403 may include receiving, for each image element (e.g., voxel), a label. The label may indicate the boundary of a structure of interest. Step 405 may include defining the boundary of the structure of interest based on the label (e.g., by image voxels).

In one embodiment, step 407 may include training a statistical model (e.g., a nearest neighbor classifier, a random forest classifier, etc.) to predict the probability that a voxel or a point at an image location (e.g., the center of an image sub-region) comprises a boundary point. The probability may be determined based on a local image descriptor associated with the voxel or the point. The local image descriptor may be provided by the label (e.g., of step 403). In other words, one or more of the training images may include detected image-derived features. Each of the image-derived features may have a corresponding label and point location indicator (e.g., a point may be located at the center of an image sub-region). The label may indicate whether the point constitutes a boundary point of the structure of interest (e.g., the point constitutes image background or the point constitutes a boundary of the structure of interest).

Each of these associations or pairings between image-derived features and labels may constitute "training examples" produced from the training images. The training phase may include determining and/or receiving the training examples. The training phase may include training the statistical model to predict a label for a new image, based on an image descriptor (e.g., an image-derived feature). The image descriptor may be associated with a location (e.g., a voxel) of the new image, and the label for the new image may include a likelihood (e.g., probability) that the location of the new image constitutes a boundary of the object of interest.

FIG. 4B is a block diagram of an exemplary method 410 for a testing phase that may provide a probabilistic segmentation based on local image descriptors, according to one embodiment. In one embodiment, step 411 may include receiving an image in an electronic storage medium (e.g., hard drive, network drive, cloud drive, mobile phone, tablet, database, etc.). The images may include image may include a representation of a portion of a patient's anatomy.

In one embodiment, step 413 may include predicting the probability that a location (within a local image region of the received image) comprises a boundary point (e.g., of the patient's anatomy). For example, step 413 may include predicting the probability that the location is a boundary point of the object, using the trained statistical model (of method 400). In one embodiment, step 413 may include defining a region around a likely boundary point to be a region of uncertainty. Alternately or in addition, step 413 may include applying a shape-fitting model to determine the object boundary. The application of the shape-fitting model may have the goal of covering the space around a segmentation boundary. For example, one scenario may include applying a shape-fitting model to cover the entire space around a segmentation boundary. In one embodiment, applying the shape-fitting model to determine the object boundary may be based on the boundary points in which the regions of uncertainty may lie along the normal directions of the object boundary. In the case of a medial axis representation (e.g., a surface described by a curve, a set of perpendicular rays, and distances along the ray), uncertainties may be in the direction of the respective rays. The spatial distribution of the probability map in the uncertainty region may be summarized as an uncertainty score. For instance, the standard deviation of the probability map may be computed within the region to determine an uncertainty score. Alternatively, another statistical classifier could be trained to map uncertainty regions to an uncertainty score.

In one embodiment, step 415 may include generating and outputting a complete segmentation boundary of the object and the associated uncertainty values to an electronic storage medium (e.g., hard drive, network drive, cloud drive, mobile phone, tablet, database, etc.) and/or display. The object may include at least a portion of the patient's anatomy.

Thus, a segmentation may render various segmentation boundary locations of varying degrees of accuracy. The present disclosure is directed to providing information on the statistical confidence (or statistical uncertainty) of a segmentation by predicting a probability distribution of segmentation boundary locations. The probability distribution may include a probability density function. One embodiment of predicting a probability density function may include two phases: a training phase and a testing phase. An exemplary training phase may include recognizing patterns of statistical uncertainty from a collection of parameterizations or segmentations, and storing the recognized patterns. An exemplary testing phase may include using the recognized patterns to predict a probability density function of an image segmentation of a new image. In one embodiment, the training phase may include training a statistical model or system to recognize the patterns of uncertainty in segmentations. The testing phase may include applying the trained statistical model to a new image, segmentation, or object parameterization, to predict a probability density function or confidence value for the segmentation/parameterization. The probability density function or confidence value may be used in improving the accuracy of segmentation(s), models made from segmentation(s), or analyses performed using such models.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of performing probabilistic segmentation in anatomical image analysis, the method comprising:
    receiving at least one image of a patient's anatomy;
    using the at least one image, determining a distance from a point on a centerline of an anatomical structure of the anatomy to a point on a lumen boundary of the anatomical structure;
    determining a parameterized representation of an anatomical structure of the patient's anatomy based on the received at least one image of the patient's anatomy;
    mapping a region of the parameterized representation to the determined distance;
    based on the mapping of the region of the parameterized representation of the anatomical structure to the determined distance, generating a probability distribution for a patient-specific segmentation boundary associated with the patient's anatomy;
    computing at least one statistical confidence value based on the probability distribution; and
    generating a segmentation boundary associated with the patient's anatomy based on the probability distribution and the at least one statistical confidence value.

2. The method of claim 1, further comprising:
    determining a region of the segmentation boundary associated with the at least one statistical confidence value below a predetermined threshold; and
    generating a display and/or notification of the region with the at least one statistical confidence value below the predetermined threshold.

3. The method of claim 1, further comprising:
    generating an interactive user interface or prompt based on the at least one statistical confidence value.

4. The method of claim 1, further comprising:
    predicting a physiological or biomechanical property of the patient's anatomy, based on the at least one statistical confidence value.

5. The method of claim 1, further comprising:
    segmenting the at least one image of the patient's anatomy, based on the segmentation boundary.

6. The method of claim 1, further comprising:
    generating the segmentation boundary further using surface reconstruction.

7. The method of claim 1, further comprising:
    determining a blood flow characteristic based on the segmentation boundary and the at least one statistical confidence value.

8. A system for performing probabilistic segmentation in anatomical image analysis, the system comprising:
    at least one server storing instructions for performing probabilistic segmentation in anatomical image analysis; and
    at least one processor configured to execute the instructions to perform operations comprising:
        receiving at least one image of a patient's anatomy;
        using the at least one image, determining a distance from a point on a centerline of an anatomical structure of the anatomy to a point on a lumen boundary of the anatomical structure;
        determining a parameterized representation of an anatomical structure of the patient's anatomy based on the received at least one image of the patient's anatomy;
        mapping a region of the parameterized representation to the determined distance;
        based on the mapping of the region of the parameterized representation of the anatomical structure to the determined distance, generating a probability distribution for a patient-specific segmentation boundary associated with the patient's anatomy;
        computing at least one statistical confidence value based on the probability distribution; and
        generating a segmentation boundary associated with the patient's anatomy based on the probability distribution and the at least one statistical confidence value.

9. The system of claim 8, the operations further comprising:
    determining a region of the segmentation boundary associated with the at least one statistical confidence value below a predetermined threshold; and
    generating a display and/or notification of the region with the at least one statistical confidence value below the predetermined threshold.

10. The system of claim 8, the operations further comprising:
    generating an interactive user interface or prompt based on the at least one statistical confidence value.

11. The system of claim 8, the operations further comprising:
    predicting a physiological or biomechanical property of the patient's anatomy, based on the at least one statistical confidence value.

12. The system of claim 8, the operations further comprising:
    segmenting the at least one image of the patient's anatomy, based on the segmentation boundary.

13. The system of claim 8, the operations further comprising:
    generating the segmentation boundary further using surface reconstruction.

14. The system of claim 8, the operations further comprising:
    determining a blood flow characteristic based on the segmentation boundary and the at least one statistical confidence value.

15. A non-transitory computer readable medium for use on a computer system containing computer-executable programming instructions, that when executed by a computer cause the computer to perform operations of performing probabilistic segmentation in anatomical image analysis, the operations comprising:
    receiving at least one image of a patient's anatomy;
    using the at least one image, determining a distance from a point on a centerline of an anatomical structure of the anatomy to a point on a lumen boundary of the anatomical structure;
    determining a parameterized representation of an anatomical structure of the patient's anatomy based on the received at least one image of the patient's anatomy;
    mapping a region of the parameterized representation to the determined distance;

based on the mapping of the region of the parameterized representation of the anatomical structure to the determined distance, generating a probability distribution for a patient-specific segmentation boundary associated with the patient's anatomy;

computing at least one statistical confidence value based on the probability distribution; and generating a segmentation boundary associated with the patient's anatomy based on the probability distribution and the at least one statistical confidence value.

16. The non-transitory computer readable medium of claim 15, the operations further comprising:

determining a region of the segmentation boundary associated with the at least one statistical confidence value below a predetermined threshold; and generating a display and/or notification of the region with the at least one statistical confidence value below the predetermined threshold.

17. The non-transitory computer readable medium of claim 15, the operations further comprising:

generating an interactive user interface or prompt based on the at least one statistical confidence value.

18. The non-transitory computer readable medium of claim 15, the operations further comprising:

predicting a physiological or biomechanical property of the patient's anatomy, based on the at least one statistical confidence value.

19. The non-transitory computer readable medium of claim 15, the operations further comprising:

segmenting the at least one image of the patient's anatomy, based on the segmentation boundary.

20. The non-transitory computer readable medium of claim 15, the operations further comprising, further comprising:

generating the segmentation boundary further using surface reconstruction.

* * * * *